(12) United States Patent
Bradbury et al.

(10) Patent No.: US 6,744,500 B2
(45) Date of Patent: Jun. 1, 2004

(54) IDENTIFICATION OF MATERIAL INCLUSIONS IN PULP AND PAPER USING RAMAN SPECTROSCOPY

(75) Inventors: James E. Bradbury, Wisconsin Rapids, WI (US); Donald R. Smith, Stevens Point, WI (US); Edward R. Grant, West Lafayette, IN (US); Philipp Kukura, Hamburg (DE)

(73) Assignees: Stora Enso North America Corporation, Wisconsin Rapids, WI (US); SpectraCode, Inc., West Lafayette, IN (US)

( * ) Notice: Subject to any disclaimer, the term of this patent is extended or adjusted under 35 U.S.C. 154(b) by 249 days.

(21) Appl. No.: 10/002,680

(22) Filed: Oct. 23, 2001

(65) Prior Publication Data

US 2003/0076492 A1 Apr. 24, 2003

(51) Int. Cl.⁷ .................................................. G01J 3/44
(52) U.S. Cl. ....................................... 356/301; 356/326
(58) Field of Search ................................. 356/301, 326, 356/237.1–237.6; 250/559.45, 458.1, 459.1

(56) References Cited

U.S. PATENT DOCUMENTS

| | | | |
|---|---|---|---|
| 4,066,492 A | | 1/1978 | Hill |
| 4,620,184 A | | 10/1986 | Nedstedt |
| 5,510,894 A | * | 4/1996 | Batchelder et al. ......... 356/301 |
| 5,617,206 A | | 4/1997 | Fay ............................. 356/320 |
| 5,621,522 A | | 4/1997 | Ewing et al. ............... 356/301 |
| 5,638,172 A | | 6/1997 | Alsmeyer et al. .......... 356/301 |
| 5,652,653 A | | 7/1997 | Alsmeyer et al. .......... 356/301 |
| 5,823,677 A | | 10/1998 | Forester et al. ............. 374/10 |
| 5,842,150 A | | 11/1998 | Renberg et al. ............ 702/23 |
| 5,858,021 A | | 1/1999 | Sun et al. ..................... 8/125 |
| 6,008,888 A | * | 12/1999 | Nottke et al. ................ 356/71 |
| 6,067,154 A | * | 5/2000 | Hossain et al. .......... 356/237.2 |
| 6,069,690 A | * | 5/2000 | Xu et al. ..................... 356/73 |
| 6,483,581 B1 | * | 11/2002 | Ben-Amotz et al. ....... 356/301 |
| 6,545,755 B1 | * | 4/2003 | Ishihama et al. ........... 356/301 |

FOREIGN PATENT DOCUMENTS

| | | | |
|---|---|---|---|
| WO | WO 92/22805 | * | 12/1992 |
| WO | WO 99/01750 | | 1/1999 |
| WO | 01484721 | | 12/2000 |

OTHER PUBLICATIONS

"Product Manual: 406000LXR Series Linear Positioner," Parker Hannifin Corporation, Jun. 1999.

(List continued on next page.)

*Primary Examiner*—Frank G. Font
*Assistant Examiner*—Layla Lauchman
(74) *Attorney, Agent, or Firm*—Greer, Burns & Crain, Ltd.

(57) ABSTRACT

Pulp and/or paper samples are scanned with a Laser Raman Spectroscopic probe, utilizing Raman spectroscopic technology, to generate Raman spectroscopic images of all or selected ones of the constituents and/or contaminants contained in the sample, to compare the same with a library of Raman spectroscopic fingerprints of known constituents and/or contaminants, and to identify and communicate data on all or selected ones of the constituents and/or contaminants for purposes of controlling the paper making process and/or determination of the quality of the paper produced.

10 Claims, 13 Drawing Sheets

OTHER PUBLICATIONS

"New stickies test method—statistically sound and user friendly," Heise et al., TAPPI Journal, vol. 82, No. 2, Feb. 1999.

"Standard Practice for the Separation and Examination of Stickies," ASTM Designation: D 6148–97, 1997.

"Macro Stickies Content in Pulp and Filtrates: The 'Pick–Up' Method," Voith Sulzer Technology Center, Jan. 1998.

"RMD Wet Specimen Image Analysis Methods," Verity 1A LLC, Aug. 1999.

"Review of Qualification Methods for PSA and Other Stickies," Doshi et al., 2000 TAPPI Recycling Symposium, pp. 701–711.

"Macro Stickie Content in Pulp: The 'Pick–Up' Method," TAPPI Provisional Method, T277 pm–99, 1999.

Measurements of Paper Coating Properties by NIR and Raman Spectroscopy Methods Jouni Tornberg, Juha Sumen, Janne Suhonen and Pentti Niemela; VTT Electronics; Trondheim, Jun. 7, 2000.

* cited by examiner

IDENTIFICATION OF MATERIAL INCLUSIONS IN PULP AND PAPER USING RAMAN SPECTROSCOPY

FIELD OF THE INVENTION

The invention relates to a method of and apparatus for utilization of Laser Raman Spectroscopic technology for identification of material inclusions in a cellulose matrix, particularly the identification and quantification of sclereids, shives and/or stickies that may be present in pulp or paper.

BACKGROUND

Sclereids are dense cellulosic inclusions or stone cells occurring in both hardwood and softwood fibers. When embodied in papermaking pulp in sufficient numbers, sizes and/or concentrations, they can cause a variety of problems in papermaking, calendering, coating and converting operations. In the finished paper, they may produce blemishes, reduce the visual quality of the paper, result in non-uniform reception of printing inks, etc. There are few tests available for measuring sclereid inclusions in pulp and paper and they are mainly empirical, based on human observation and manual count.

Shives are undesireable wood fiber particles that are occasionally present in a finished paper product. Shives can have disadvantageous effects on the appearance, surface smoothness, ink receptivity and other aspects of a finished paper product. Few, if any, tests are available for accurate and efficient detection of shives in pulp and paper.

Stickies are encountered in the manufacture of papers made in whole or in part from recycled paper stock due to the presence of material inclusions in the recycled stock, for example, thermoplastics, pressure-sensitive adhesives, hot melts and wax. Under the heat and pressure of the papermaking process, these materials become tacky and adhere to various components of the papermaking machinery, such as wires, felts, dryers, calendars and coaters; thus the name stickies. Stickies impair paper machine runnability, cause web breaks, are one cause of coater blade streaks, and necessitate down-time for cleaning. They also create problems in converting operations and reduce the visual quality of the finished sheet of paper. With regard to the finished sheet, it is important for recycled-paper producers and merchants to identify and quantify these materials and to characterize the quality of the recovered paper.

Several methods have been proposed for quantifying stickies in the pulp slurry at the wet end of the paper machine. Generally, these involve screening a sample of the pulp through a laboratory-screening device under controlled screening conditions to screen out macro stickies, namely stickies of a size greater than 0.10 millimeters (mm) or 0.004 inches. Smaller stickies, i.e., micro stickies, which are not deemed particularly deleterious, pass through the screen with the cellulose fibers in the pulp. The filtrate or rejects from the screen are transferred to a black filter paper. A coated paper is placed on top of the filter paper, and together they are heated and pressed under controlled conditions. When the coated paper is removed from the filter paper, the coating will be picked up by the stickies and create a contrast on the black filter paper, which allows measurement, visually or with an image analyzer, of the area and the number of the heat-set stickies. See, e.g., TAPPI Journal, Vol. 82, No. 2, February 1999, pages 143–151.

U.S. Pat. No. 5,823,677 discloses a method of detecting and identifying stickies based on infrared (IR) radiation. According to the disclosure, a temperature gradient will exist between the stickies and a reference, e.g., ambient temperature or a substrate containing the stickies, when a sample containing the stickies and the reference are allowed to cool or to warm from a first temperature to a second temperature over a controlled period of time. The temperature gradient or difference is determined by measurement of the infrared radiation of the stickies and the reference, preferably by use of a thermographic camera. Also according to the disclosure, a characteristic gradient exists for each type of stickie when allowed to lose or gain heat for the same amount of time. These characteristic gradients allow for identification of the type of stickie by the surface temperature. This gradient is a function of the rate of heat loss or gain that is uniquely associated with each type of stickie.

The method disclosed in U.S. Pat. No. 5,823,677 comprises the steps of providing a sample which contains both at least one stickie and a reference material at a first temperature; allowing the sample to change from the first temperature to a second temperature; scanning the sample with a means for measuring infrared radiation after the sample has reached the second temperature so as to sense the temperatures of said at least one stickie and the reference material; determining the temperature difference between said at least one stickie and the reference material; and identifying said at least one stickie by the temperature differential.

While the above-described methods of stickies detection are widely used in the paper industry, they do not provide adequate accuracy, precision, speed, or specific identification and quantification of material inclusions.

U.S. Pat. No. 5,842,150 discloses a method for qualitative and quantitative determination of the organic content in pulp, paper and effluents from pulp and paper mills using ultraviolet, visible, near-infrared and infrared energy techniques, including Raman Spectroscopy. Laser Raman Spectroscopy has also been used for quantifying lignin content in pulp samples.

SUMMARY OF THE INVENTION

It is an object of the present invention to provide a method of and apparatus for detecting the presence of contaminant materials in pulp and paper with accuracy, speed and precision, and with specific identification and quantification of all or selected ones of the constituents, contaminants in the pulp or paper. It is noted that as used herein the term "contaminants" is intended to broadly refer to substances whose presence are undesirable in paper or pulp products, with examples including but not limited to sclereids, shives, stickies, foreign substances, and the like.

It is in particular an object of the invention to provide a method of and apparatus for detecting the presence of sclereids, shives, and the like in pulp and paper, and the presence of stickies and the like in pulp and paper made in whole or in part from recycled stock, and to do so with greatly enhanced speed, accuracy and precision, and with specific identification and quantification of each stickie, sclereid, and shive substance present in the pulp or paper.

A further object of the invention is to utilize laser Raman spectroscopic technology, in combination with computer science, to provide precise identification and quantification of the constituents and contaminants in pulp or paper, especially pulp and paper made from or containing recycled stock.

A further object of the invention is to provide for high-speed laser Raman spectroscopic scanning of pulp and paper samples, transmission of Raman images of the constituents and/or contaminants in the samples to a computer, comparison of the transmitted images to a library of Raman fingerprints in computer memory, and communication to papermaking personnel of the identity, quantity and location in the sample of all and/or selected ones of the constituents and/or contaminants present in the sample.

Raman spectroscopic technology is capable of producing a distinctive "image" of each substance submitted for spectroscopic examination and each image is different from the images of all other substances. It is noted that as used herein, the term "image" as used with respect to spectroscopic technology is intended to broadly refer to data output from a spectrometer with or without subsequent processing. By way of example, an "image" may comprise a spectrum or other imagery, fingerprint, vector data, attribute identifier or other signal by which one substance may be distinguished from another by Raman technology. In effect, the technology produces a fingerprint individual to each substance, just as the fingerprint of each human being is distinctive and different from the fingerprints of all other human beings. While the differences may be slight, there is nevertheless sufficient difference to distinguish one human fingerprint from all other human fingerprints. So too with Raman spectroscopy. Though the differences between Raman images may be slight, the differences are sufficient to distinguish each substance from all other substances, i.e., each substance has its own Raman fingerprint.

Raman spectroscopy does not require a color or black and white contrast between the constituents of and contaminants in a pulp or paper sample and therefore is not limited to the meager results of prior art techniques. Moreover, it is not limited to simply distinguishing contaminants from cellulose, it is capable of specifically identifying each contaminant substance and distinguishing varieties of contaminants from one another.

In accordance with the present invention, Raman technology is employed, first, to distinguish foreign substances, e.g., contaminants and other undesirable substances, from desired constituents of pulp or paper, primarily cellulose fibers, and second, to identify each of the foreign substances, to distinguish the foreign substances one from the other and to quantify the amount of each of the contaminants in the pulp or paper sample.

The apparatus employed pursuant to the invention to achieve the foregoing objectives is comprised principally of a Raman spectrograph including a Raman spectroscopic probe and a coherent light source for feeding high-intensity laser light to the probe. The probe contains optical assemblies for concentrating coherent light onto a pulp or paper sample and for receiving back scattered light from the sample and feeding back scattered light images to the spectrograph which disperses the light to generate a spectrum for transmission to a computer and analysis. The sample is mounted on a scanning table. The invention further comprises translating means for causing relative translation between the scannable surface and the spectrometer. Preferably, the translating means comprise a translating device such as a motor, gears, drives and the like for translating the scanning table along the X and Y-axes of the sample. The translating device is capable of high-speed movement with substantially instantaneous stop and go characteristics and is capable of being programmed through a controller for movement in pre-selected sample-scanning patterns. Control means are provided for controlling the translating means as desired. Preferred control means comprise a processor based controller, such as a computer or the like.

The movements of the scanning table are coordinated with energization of the coherent light source via the computer. Scanning of the sample may be continuous, via continuous scan or stroboscopic circuitry, or intermittent, via trigger scan circuitry, so that the coherent light source is triggered on at each pause in the intermittent travel of the scanning table and sample. The scan may be a simple back and forth scan of most or all of the surface of the sample, or the scan may be predicated on theories of statistical analysis for producing a statistically-acceptable Raman examination of the sample.

The method of the invention, in a first aspect, comprises establishment of a library of Raman spectrographic fingerprints of the constituents and/or the contaminants or other substances anticipated to be present in the pulp or paper samples to be examined. Each constituent and/or contaminant and/or other substance is identified and subjected to Raman spectroscopic examination and its identity and spectroscopic vector or Raman fingerprint inputted to computer memory.

As scanning of a sample occurs, the computer compares the Raman images transmitted to it by the spectrograph to the library of Raman fingerprints stored in computer memory and, in synchronism with the movements of the scanning table and the sample, generates a map of the sample illustrating the location and area of contaminants, especially the location and area of stickies, shives, and sclereids. In addition, the computer identifies, computes and communicates, via X-Y coordinates, the location, identity and amount of each of the contaminants. If a foreign substance in the sample is discerned by the Raman spectroscope, and its Raman image cannot be matched with a Raman fingerprint in memory, the substance is reported simply as an unknown. Since the location (X-Y coordinates) and area of the unknown has been identified on the sample map, the substance can be removed from the sample, subjected to physical and/or chemical analysis, and its identity and Raman fingerprint added to the Raman fingerprint library.

By virtue of the above-described method and apparatus, the identity and quantity of constituents and/or contaminants and/or foreign substances in pulp and paper, particularly the identity and amount of each variety of sticky, sclereid and/or shive present in pulp or paper, can be speedily determined and communicated to paper makers and merchants for purposes of enhancing control over the papermaking process and for purposes of ascertaining the print quality and other characteristics of the paper produced.

The foregoing and other objects and advantages of the invention will become apparent to those of reasonable skill in the art from the following detailed description as considered in conjunction with the accompanying drawings.

DETAILED DESCRIPTION OF PREFERRED EMBODIMENTS

The following is a detailed description of embodiments of the invention presently deemed by the inventors to be the best mode of carrying out their invention.

Figure 1:
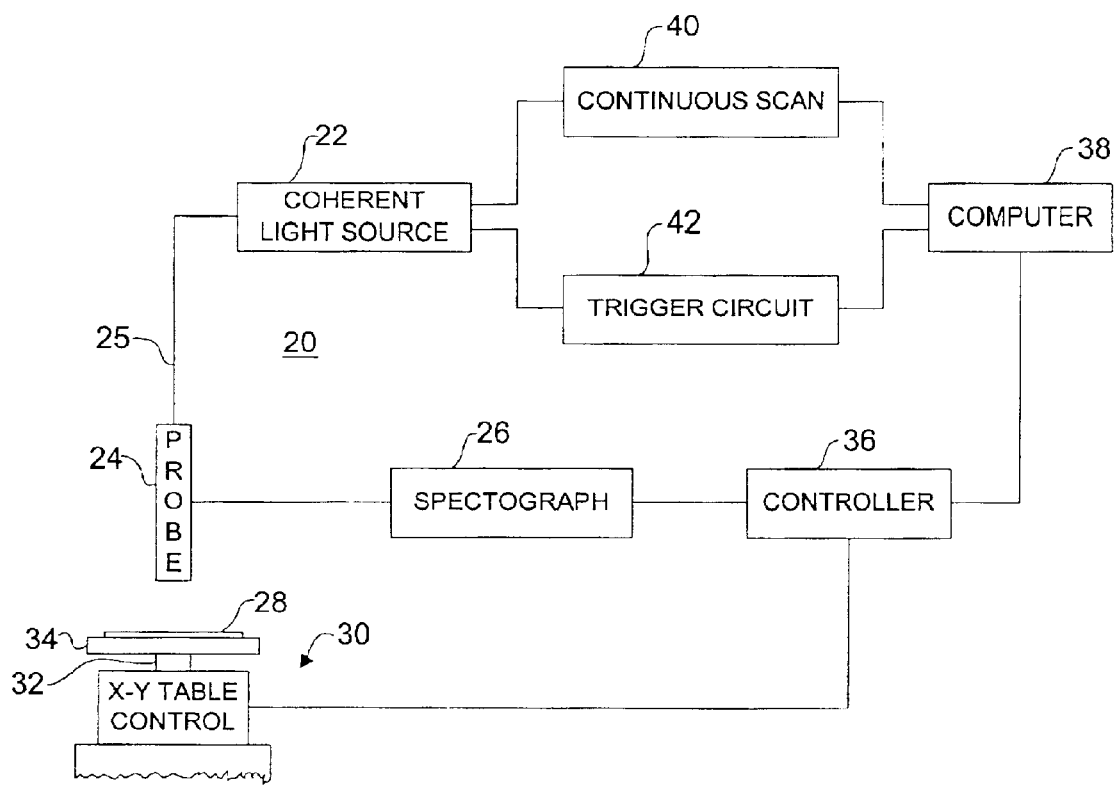
FIG. 1 is a schematic illustration of a preferred embodiment of the apparatus provided by the invention for identification of contaminants in pulp and paper.

An apparatus preferred for practice of the invention is depicted schematically in FIG. 1. A laser Raman spectroscope, indicated generally at 20, is comprised of a coherent light source 22, a sample examining or analyzing probe 24, an umbilical 25 connecting the source to the probe, and a Raman image processor or spectrograph 26 connected to an output from the probe. The probe 24 contains optical assemblies for focusing coherent light from the source onto a sample and for receiving back scattered light from the sample and feeding the back scattered light to the image processor 26. The processor in turn feeds the spectral images to a computer 38. A Raman spectroscope and its mode of operation are illustrated and described in detail in International Publication No. WO 99/01750, published Jan. 14, 1999, the disclosure of which is incorporated herein by reference.

A sample mounting table 28 comprises a flat horizontal surface for reception of a wet or dry sample of pulp or paper. The Raman probe 24 is preferably mounted in a stationary, substantially vertical position above the table for scanning the sample on the table. The horizontal surface of the preferred table is scannable, i.e., translatable along X and Y-axes, to facilitate scanning by the probe of the entire area, or selected areas, or selected points on the surface of the sample. It is noted that equivalent translating means could be provided to provide relative translation between the spectrometer laser and the sample. For example, means could be provided for translating the spectrometer probe along one or more axes. By way of a more particular example, translating means could be provided for moving the spectrometer probe along one axis and for translating the sample along a second axis.

The Raman probe 24 may also be equipped with microscopic objectives or optical assemblies known in the art for examining and analyzing the sample along the Z-axis, i.e., through the thickness dimension of the sample, thereby to feed back a three dimensional Raman image of the sample and/or data concerning the cross-sectional characteristics of the sample, for example, the thickness and composition of a paper substrate and the thicknesses and composition of coatings applied to the substrate. Providing a wet sample and/or wetting the sample before scanning can improve performance of Z-axis scanning.

Figure 2:
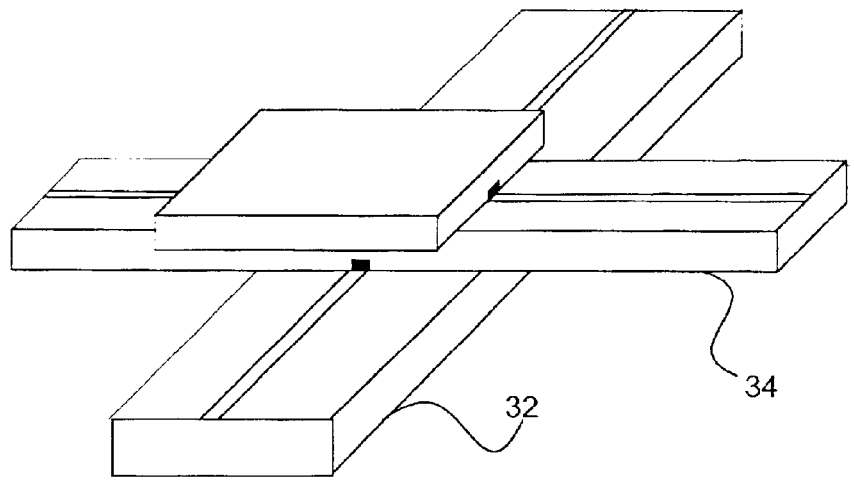
FIG. 2 is a perspective view of an X-Y translation device included in the apparatus of FIG. 1.

A translation mechanism 30 mounted below the sample table 28 supports the table for translation along the X and Y-axes of the table and a sample mounted on the table. The mechanism, a portion of which is illustrated in perspective in FIG. 2, includes a pair of rails 32 and 34 mounted at right angles to one another. Each rail contains a flexible conveyor and a linear magnetic motor for reciprocating the respective conveyor. One rail 32 is connected to a stationary support, such as a control box. The other rail 34 is mounted on the conveyor of the rail 32 and the support table 28 is mounted on the conveyor of said other rail 34. The linear magnetic motors drive the conveyors at constant speed with substantially instantaneous stop and go, thereby providing for high-speed scanning of the sample mounted on the surface of the table 28. A translation mechanism preferred for practice of the invention is the 406000LXR Linear Positioner produced by Parker Hannifin Corporation of Irvine, Pa.

The translation mechanism 30 also comprises control means for controlling the translation as desired. A preferred control means comprises a programmable processor based controller, which may comprise for example a separate computer attached to the translation mechanism 30, a dedicated special purpose controller connected to the mechanism 30, a controller housed within the mechanism 30, or the like. The mechanism 30 is programmable to provide substantially any scanning pattern desired. The scan may be continuous or discontinuous, i.e., intermittent. The sample table may be of substantially any size and shape desired. At present, a table fourteen inches square has been found suitable. The sample itself may be the same size as the table or any smaller size, for example, eight inches by eight inches. A typical scan would, for example, start at the upper left corner of the sample and continue along the X-axis to the upper right-hand corner of the sample, be indexed one "notch" down along the Y-axis, then reciprocated back along the X-axis from the right edge of the sample to the left edge, again indexed down one notch along the Y-axis, and this pattern of movement repeated until the entire surface area of the sample has been passed under and subjected to examination by the Raman probe 24. Those knowledgeable in the art will appreciate that a "notch" as used herein is intended to broadly refer to a measure of laser spot size.

Other patterns of sample movement and Raman examination may be devised as desired for optimum sample examination and speed, for example, patterns predicated on theories of statistical analysis.

With the scanning table moving either continuously or intermittently, the probe 34 can be triggered intermittently to examine either selected areas or all areas of the sample. The probe (laser) can for example have a field of vision of 0.5 mm in diameter and can be pulsed at 0.1 second intervals, and the table moved fast enough to match the pulse speed. Full surface coverage and complete identification of the samples constituents and/or contaminants will produce a complete chemical identification map, in which the locations and areas of each chemical are marked by X-Y coordinates.

For greater speed of scanning, statistically or randomly selected areas, e.g., a five percent to twenty-five percent coverage pattern, could be scanned to map the surface areas where the measurements were taken.

Alternatively, the entire surface of the sample may be rapidly pre-scanned in the continuous scan mode to log discreet positions that are suspect and the probe thereafter returned to the suspect positions for a complete chemical analysis. This would provide information about all of the inclusions without taking the time to analyze all of the matrix (cellulose) positions. For the pre-scan, a specific spectrum characteristic of the cellulose matrix can be established, sampled spectra sufficiently different from the matrix logged by X-Y coordinates and stored in memory, and these X-Y coordinate positions thereafter subjected to full Raman spectroscopic examination.

By way of further example, timesavings can be achieved by first scanning relatively large cells to determine if a non-paper, i.e., foreign, material is within the large cell, and then returning to the cells with foreign materials to perform a more detailed scan and analysis. By way of illustration, large cell of a size on the order of 0.5 by 5 mm may be scanned and "flagged" for re-scanning if a foreign material is detected. Upon re-scanning, the larger cell may be subdivided into a plurality of smaller cells of a size of the order of 0.5 by 0.5 mm to more accurately map the location and determine the size and identity of the foreign material. The size of the cells may be varied, and that the cell sizes discussed herein are for purposes of illustration only.

It is noted that as used herein the terms "foreign material" and "material" are intended to broadly refer to substances identifiable in a sample against a second background material in the sample. By way of example, "materials" identified through the practice of the invention may comprise any of a variety of substances that differ in chemical composition from the background pulp or paper. Those knowledgeable in the art will appreciate that there are a wide variety of materials that may desireably be identified in pulp or paper making. Particular materials for purposes of illustration only include paper additives such as talc, clay, shives, stickies, sclereids, or the like.

Movement of the scanning table 28 by the mechanism 30 is governed by a controller 36 that in turn is governed by the computer 38 which also governs the coherent light source 22. The computer 38 is programmable to establish whether the scan is to be continuous or intermittent; and if continuous to energize the coherent light source by a continuous scan or stroboscopic circuit 40, and if intermittent, to time energization of the laser or coherent light source 22 in synchronism with movement of the sample table via a trigger circuit 42. If desired, the continuous scan and trigger circuits 40 and 42 can be embodied in a single module within the skill of the art.

Laser Raman spectroscopic technology produces a distinctive image of each substance submitted for spectroscopic examination and each image is different from the images of all other substances. The technology produces a vector or Raman fingerprint individual to each substance. While the differences between Raman images may be slight, the differences are sufficient to distinguish each substance from all other substances, i.e., each substance has its own Raman fingerprint.

Figure 3:
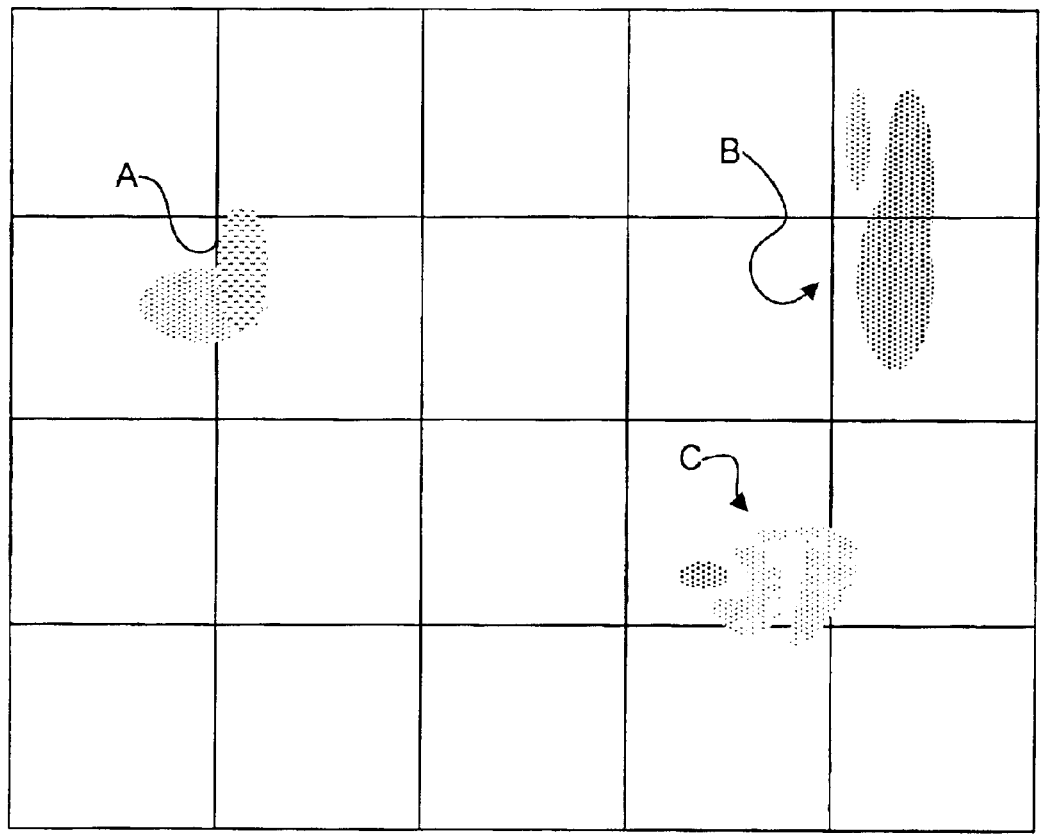
FIG. 3 is a sample map illustrating the presence of contaminants in a pulp or paper sample.

In accordance with one aspect of the present invention, Raman technology is employed, first, to distinguish foreign substances, e.g., contaminants and other undesirable substances from the desired constituents of pulp or paper, primarily the cellulose fibers, and second, to identify each of the foreign substances, to distinguish the foreign substances from one another and to identify and quantify the amount of each of the foreign substances in the pulp or paper sample. In the first instance, the apparatus and scanning techniques above-described will enable a properly programmed computer 38 to produce a sample map identifying by X and Y-coordinates the location, size and shape of each contaminant, or each of the selected contaminants, discerned in the sample by the apparatus of FIG. 1. FIG. 3 illustrates a more or less typical sample map containing contaminants of different size and shape at A, B and C. If the proportion of contaminants and undesirable substances to the desired constituents, as revealed by sample map area comparisons, is unacceptably high, remedial steps may promptly be undertaken as desired. Identification of the offending contaminant(s) will facilitate tracing the problem back to its source and thus provide a means of rapid testing and control.

In addition, the images of the contaminants and undesirable substances transmitted by the probe to the processor and the computer will enable the computer, by comparison of the images to an established library of Raman fingerprints, to identify each of the contaminants individually, or if no fingerprint match is found by the computer, to identify and quantify the substance as an unknown.

The present invention preferably further comprises quantifying the contaminant, impurity, foreign substance or the like. The size of the contaminant may be determined in units of area, volume or mass. For example, a volumetric quantity may be estimated based on its area and depth, and/or signal intensity, of the detected material. Further, if a material is identified through matching of its fingerprint with a known fingerprint from a library, the material density may be available, in which case a volume can be converted to mass.

The Raman spectroscopic probe, for example at each energization of the laser or coherent light source, will take a "screen shot" or "picture" of the portion of the sample within the field of vision of the probe. It is noted that the terms "screen shot" and "picture" as used herein in this context are intended to broadly refer to concepts of sampling, such as obtaining data vectors, arrays, matrices, spectra, signals, or the like. The screen shot transmitted by the probe to the processor may consist of the image or Raman fingerprint of a single substance or the images/Raman fingerprints of a plurality of substances. The image processor and the computer may be programmed to identify and quantify all of the transmitted images or they may be programmed to recognize, identify and quantify just one image, i.e., the Raman fingerprint of just one stickie, or selected images, e.g., the Raman fingerprints of each of several stickies, sclereids, or shives, or combinations of one or more of these.

Figure 4:
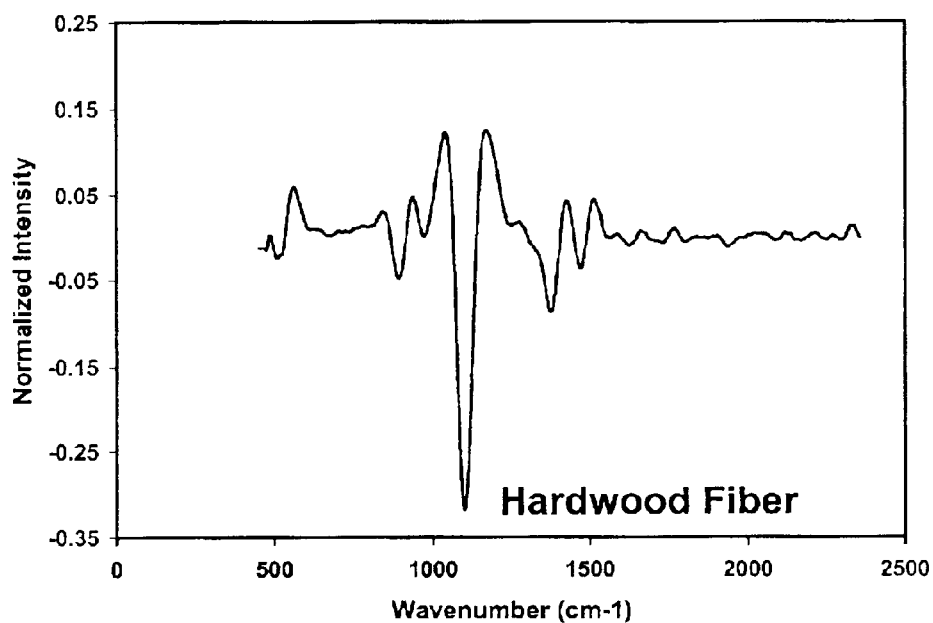
FIG. 4 illustrates the Raman fingerprint of a hardwood fiber.
Figure 5:
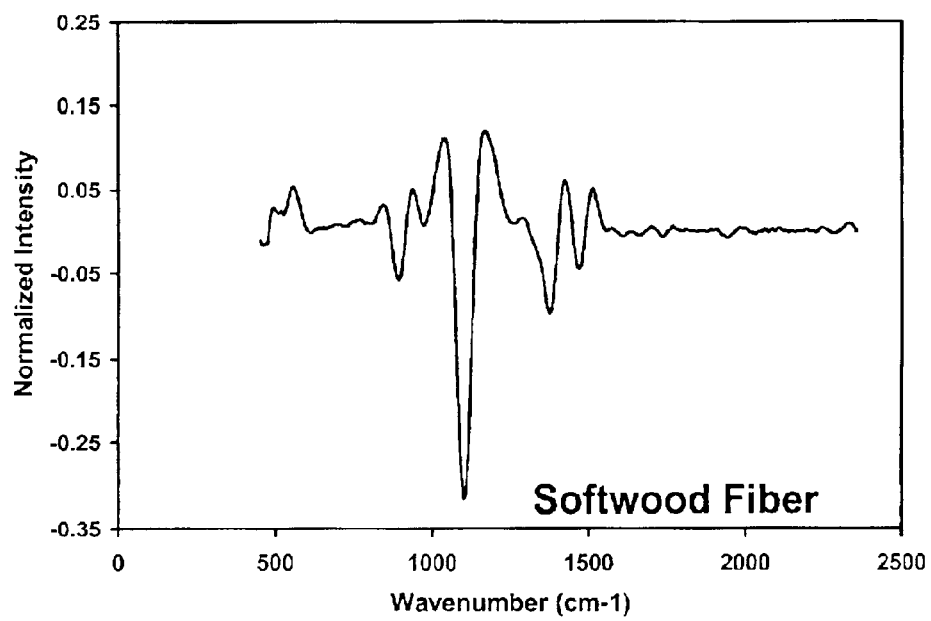
FIG. 5 illustrates the Raman fingerprint of a softwood fiber.
Figure 6:
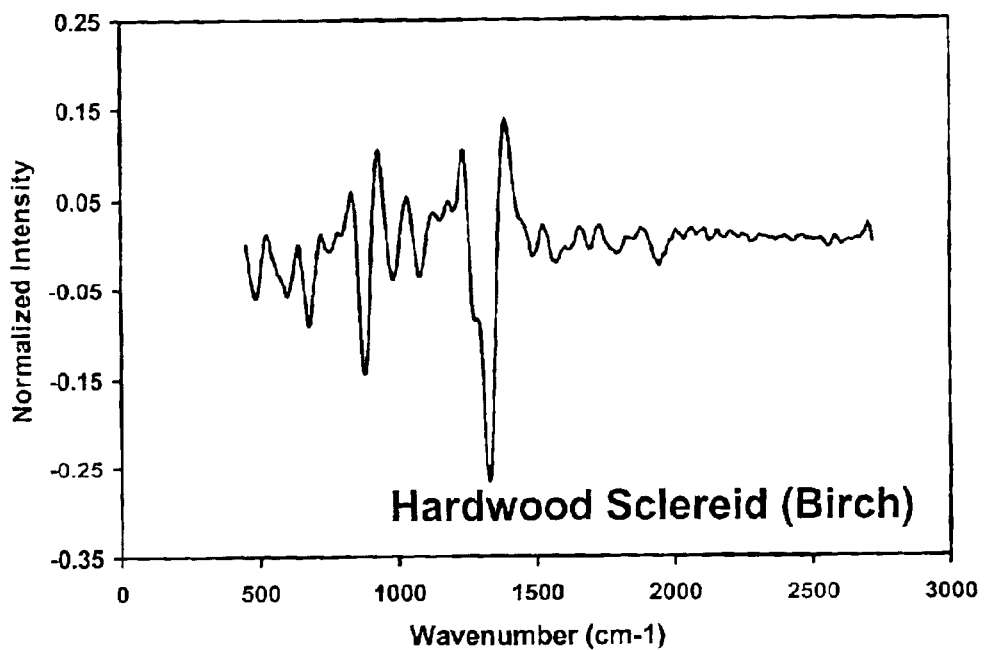
FIG. 6 illustrates the Raman fingerprint of a hardwood sclereid.
Figure 7:
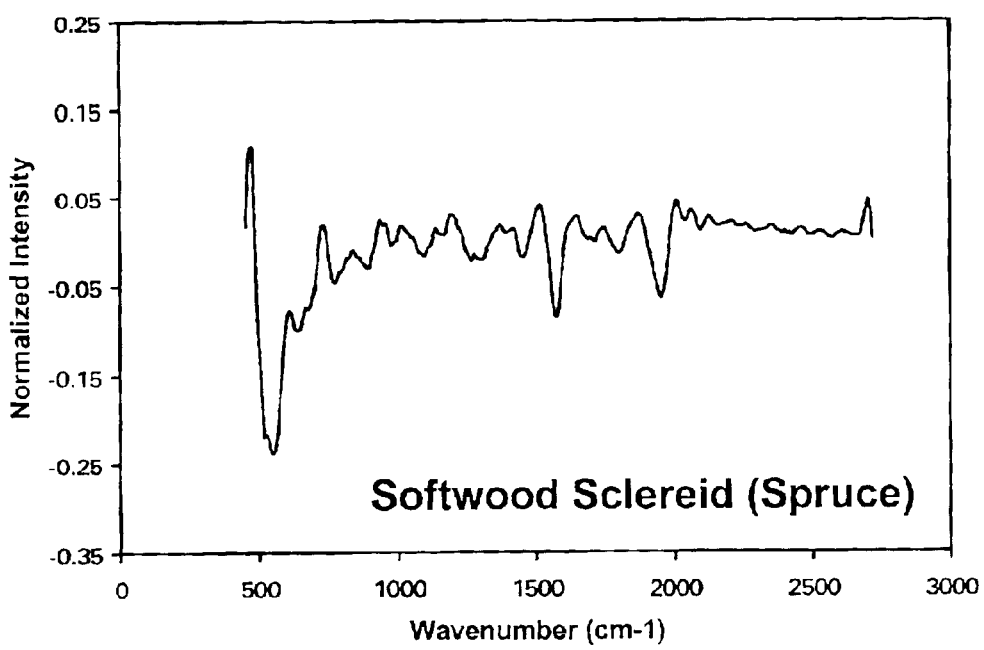
FIG. 7 illustrates the Raman fingerprint of a softwood sclereid.
Figure 8:
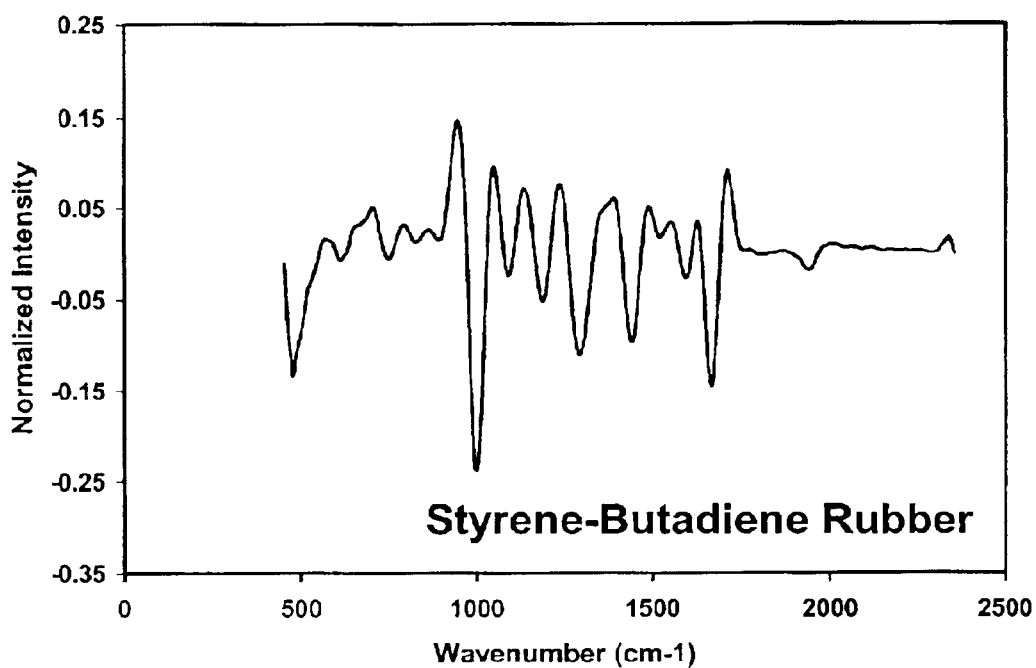
FIG. 8 illustrates the Raman fingerprint of a styrene butadiene rubber stickie.
Figure 9:
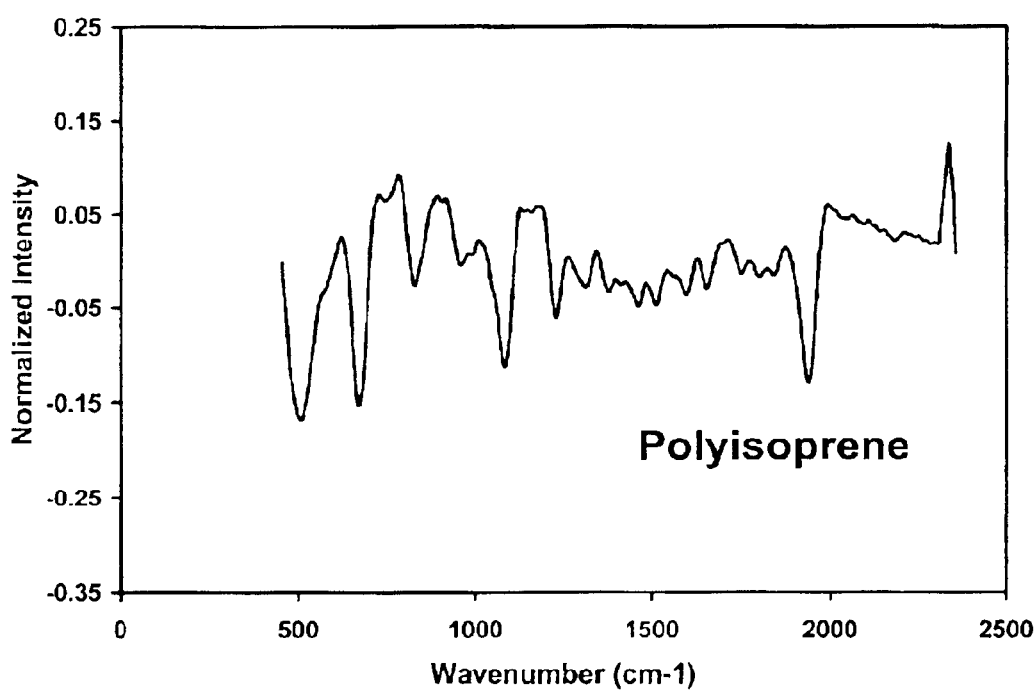
FIG. 9 illustrates the Raman fingerprint of a polyisoprene stickie.
Figure 10:
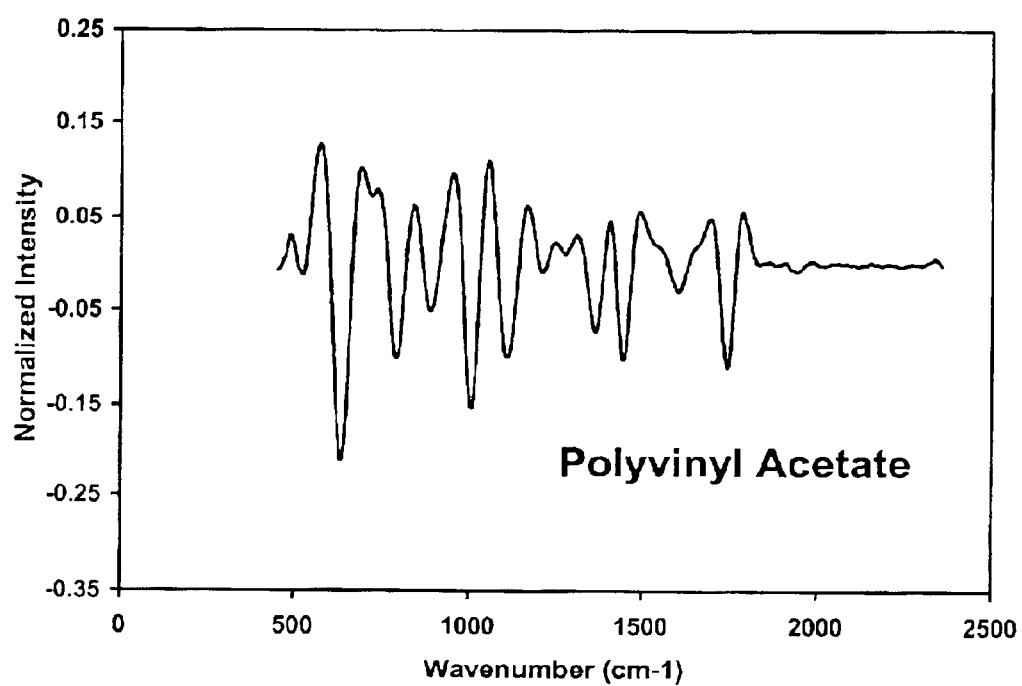
FIG. 10 illustrates the Raman fingerprint of a polyvinyl acetate stickie.

Representative Raman fingerprints are illustrated in FIGS. 4–10. The Raman fingerprints of a hardwood fiber and a softwood fiber are shown in FIGS. 4 and 5. The Raman fingerprints of a hardwood sclereid and a softwood sclereid are shown in FIGS. 6 and 7. The Raman fingerprints of several stickie substances are shown in FIGS. 8, 9 and 10. As above noted, though the differences between the Raman fingerprints may be slight, they are sufficiently different to be distinguished from one another and identified by computer match.

The Raman fingerprints of these and other known pulp constituents and contaminants are fed into a library maintained and held in computer memory. If an unknown is encountered with sufficient frequency, it can be segregated from the sample, at the indicated X and Y coordinates, and subjected to physical and/or chemical analysis and its identity and Raman fingerprint added to the library as a known.

For examination of finished paper products or partially-finished paper products, e.g., before calendering or coating of the same, one or more samples of the product may be subjected to Raman spectroscopic examination in the manner above-described for purposes of determining the quality of the paper, the manner in which it should be further processed and/or the manner and purposes for which the paper should be marketed.

For examination of pulp, a sample of the make down slurry or furnish to the paper-making machine is screened in the same manner as described in the background portion of this application to screen or filter out macro contaminants, for example, macro stickies, and the filtrate is transferred to a sheet of filter paper. However, there is no need in practice of the present invention to further process the sample to develop a color contrast or a black and white contrast between the filter paper and the stickie. In practice of the invention, the contaminant containing filter paper, either wet or dry, is transferred directly to the sample table 28 for Raman spectroscopic examination.

The process of subjecting samples to examination and communicating the results of the examination, with specific identification and quantification of each contaminant in the sample, is carried out within an established time frame of thirty minutes or less based on a nominal sample size of about 8" square, and with greater accuracy, greater detail and significantly greater scientific precision than heretofore available.

It will be appreciated that embodiments of the method of the invention lend themselves well to practice in the form of computer program products. Accordingly, it will be appreciated that additional embodiments of the present invention comprise computer program products for execution by a processor based device. For example, a computer program product of the invention may comprise computer executable instructions in the form of program instructions that have been compiled into a machine readable format and stored in a computer readable medium such as a magnetic, optical or other memory; embedded in circuitry or micro-circuitry, or the like. The program instructions may be executed by a processor based device such as a computer or laboratory instrument. Indeed, "computer" as used herein is intended to broadly refer to any processor based device capable of executing instructions. FIGS. 11 and 12 are useful for describing embodiments of computer program products of the invention. It will also be appreciated that these flowcharts may likewise be of use in describing method embodiments of the invention.

Figure 11A:
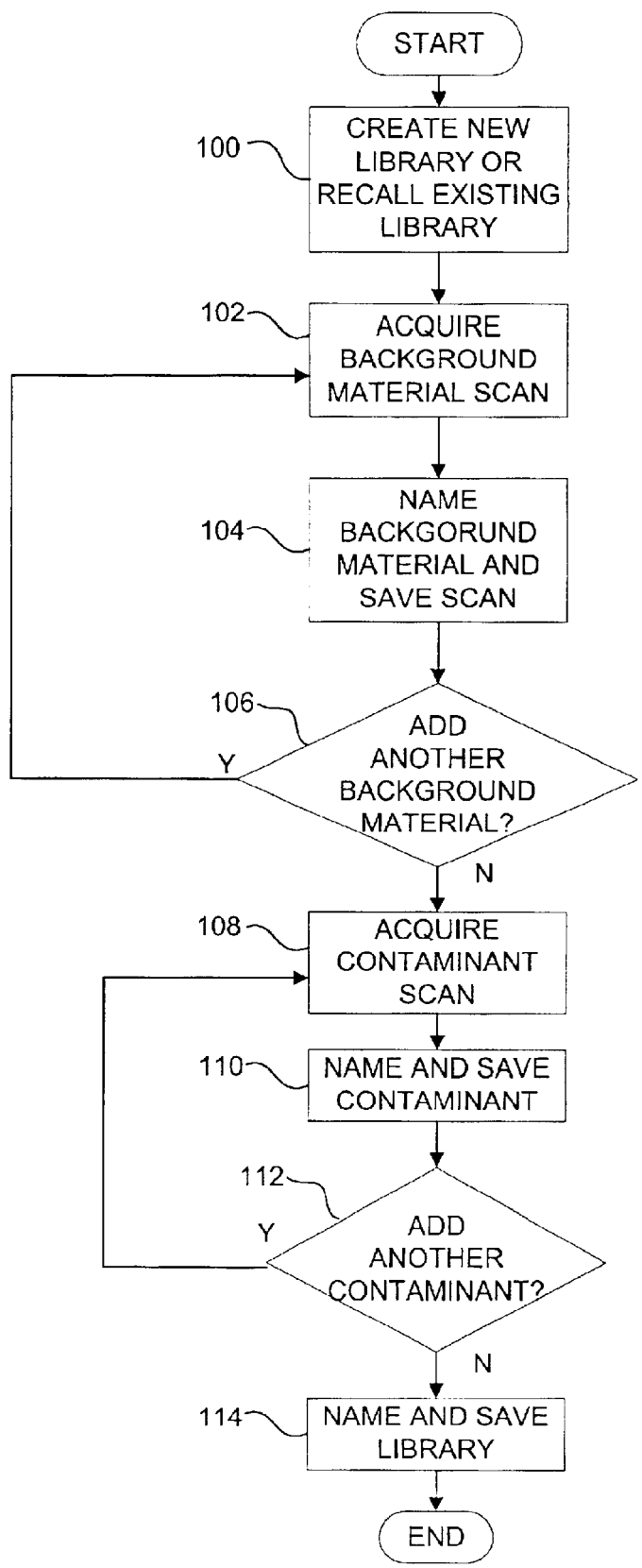
FIGS. 11(a) and (b) are flow charts illustrating a general embodiment of a method and computer program product of the invention.
Figure 11B:
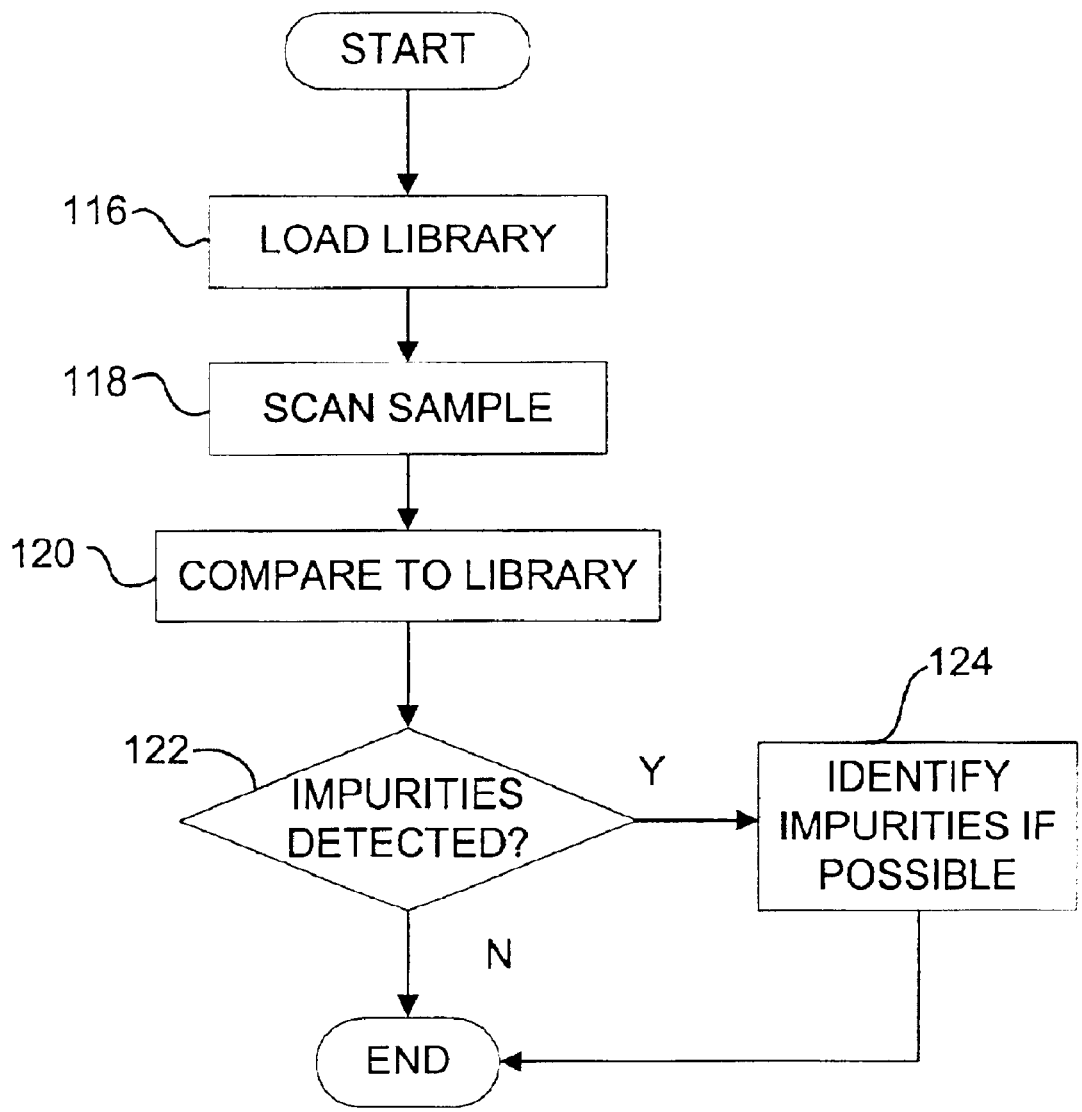

FIG. 11 is a flowchart illustrating a general embodiment of a method and computer program product of the invention. With reference to FIG. 11(a), an initial method and program step is to create a new library (block 100). "Library" as used herein is intended to broadly refer to a collection of individual data members, and in context may refer to a collection of Raman fingerprints. Preferably, some library data members will comprise "background" materials and other members such as stickies, sclereids, shives, and the like, will comprise "contaminant" members. A "background material" may be considered to be a pure or otherwise standard material substantially free of impurities. By way of example, if a method of the invention is practiced to detect impurities in paper or pulp, a background material may comprise the paper or pulp material in a state substantially free of any impurities.

The method and program embodiment further comprise scanning the background material with the spectrometer (block 102), and naming and saving the resultant data set (block 104). Multiple background materials may be scanned (block 106), if for instance multiple grades or qualities of pulp or paper were of interest. Contaminant scans are also obtained (block 108), named, and saved in the library (block 110). Multiple contaminant scans may be obtained (block 112). The library containing the background and contaminant data members may then be named and saved (block 114).

Following creation of one or more libraries, scans may be performed on samples. Initially, a library is loaded (block 116), and a sample scanned with the spectrometer (block 118). The resulting data from the sample scan may then be compared to the library data members (block 120) to determine whether impurities are present (block 122). If so, the images can be compared to individual contaminant data from the library to determine an identity of the contaminant (block 124). If no match is determined, a contaminant may be simply identified as "unknown".

With the general flow charts of FIG. 11 having now been presented, a more detailed method and program embodiment of FIGS. 12(a)-(e) may be described. Initially, an indication is made that a new library is to be created, or an existing library is to be edited (block 200). A library may desirably be edited, for instance, if additional background or contaminant members are to be added. A series of steps are then undertaken to create, name, and store background material spectrometer data scans (dashed line block 202). A sample of background material such as paper, pulp, or the like is scanned with the spectrometer (block 204). The resulting data is then reviewed to determine if the scan is acceptable (block 206). As will be appreciated by those knowledgeable in the art and by way of example, a scan may, for example, be unacceptable if the level of reflectance is too high and the data is saturated. If the scan is unacceptable, adjustments may be made to the spectrometer settings (block 208) and the sample re-scanned.

Once an acceptable scan has been obtained, the raw data is converted to a vector format (block 210). As will be appreciated by those knowledgeable in the art, "raw" spectrometer data is desirably converted for ease of manipulation to vector data, and is further preferably normalized so that data may be more accurately compared from run to run. For more invormation regarding the use of data in a vector format in association with spectrometry, reference is made to the International Publication No. WO 99/01750, published Jan. 14, 1999, which has been incorporated herein by reference. The converted and normalized vector data member is then named (block 212) and added to the library (block 214). A determination is then made as to whether sufficient output data has been obtained for the sample (block 216). By way of example, several scans of the sample may be useful to average out noise and other inconsistencies in the data. Generally, it has been discovered that 4–5 scans are practical for obtaining suitably averaged data. Similarly, it has been discovered that of the order of 20 scans may be too many, with the result that data becomes too "artificially sensitive." Additional background materials may also be scanned and added to the library (block 218).

Figure 12A:
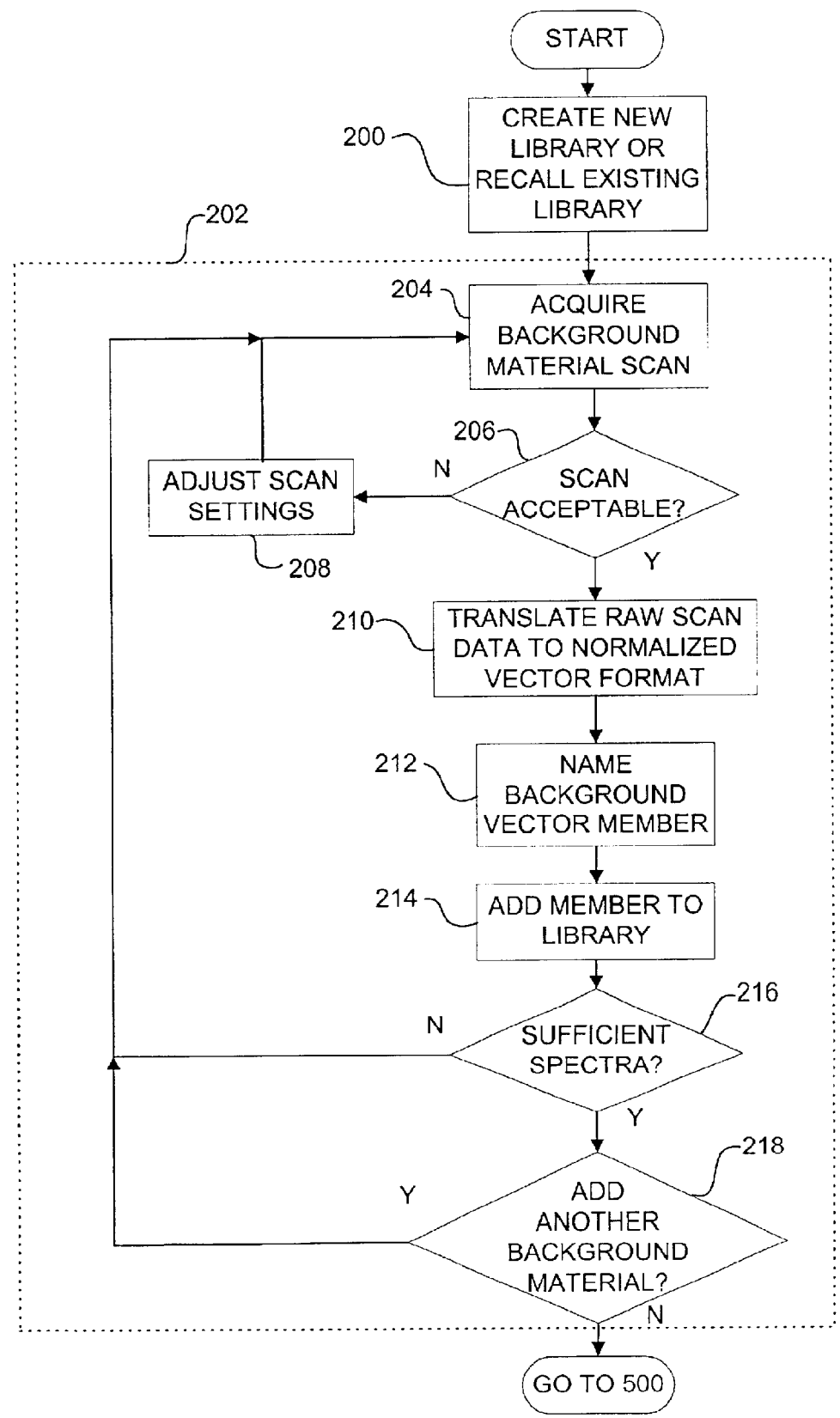
FIGS. 12(a)–(e) are flow charts illustrating an additional embodiment of a method and computer program product of the invention.
Figure 12B:
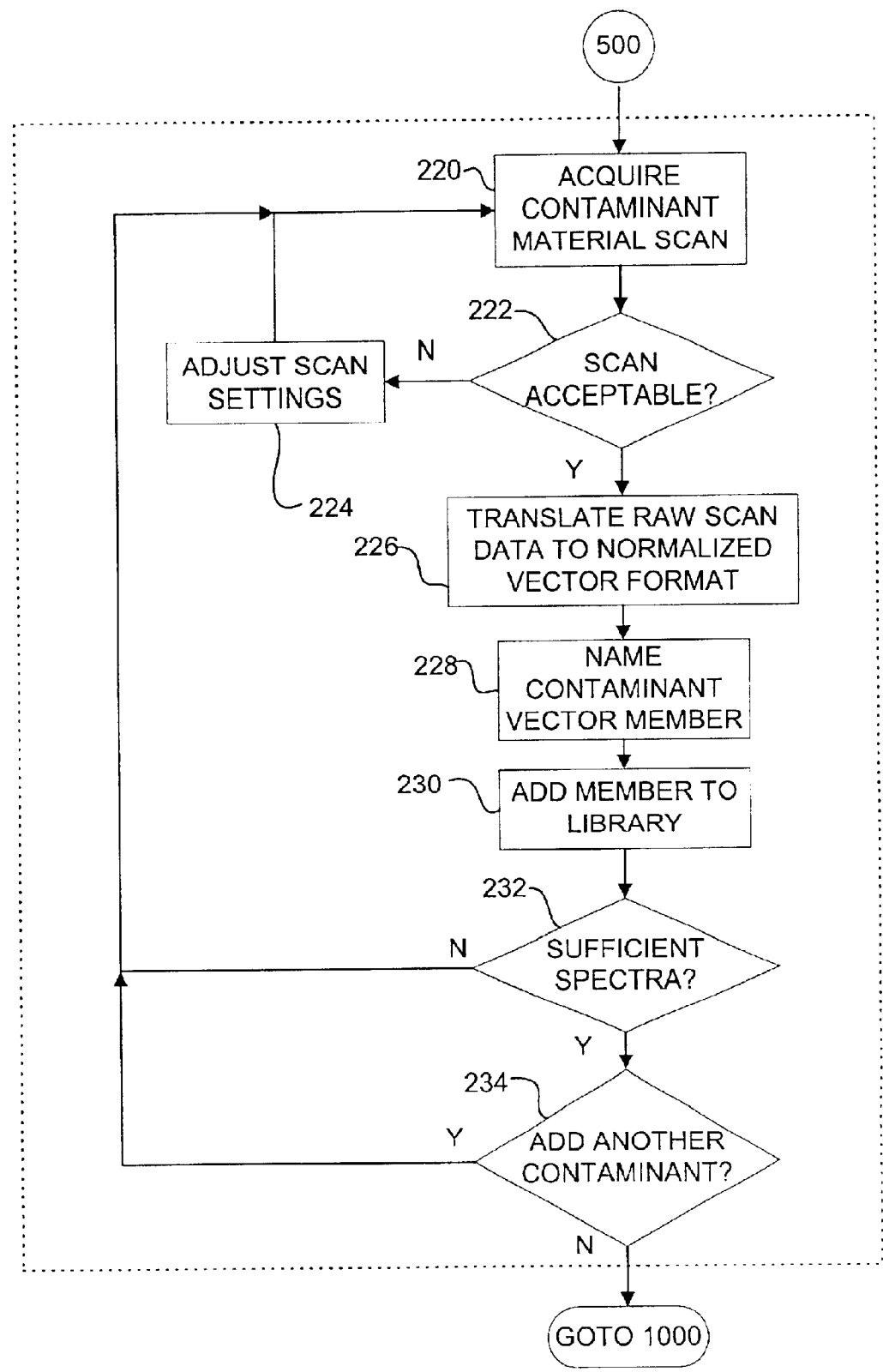

Spectrometer scan data for impurities will be obtained in addition to data for background material. With reference to FIG. 12(b), a contaminant is scanned with the spectrometer, with adjustments made to the spectrometer as required until acceptable data is obtained (blocks 220, 222, 224). As will be appreciated by those knowledgeable in the art, the spectrometer settings should be consistent between background and contaminant scans, so adjustments are preferably only made during the background or contaminant scans, but not during both. Once obtained, the raw scan data is converted to normalized second derivative vector data (block 226), and the vector data named and saved to the library (blocks 228–230). Scans are repeated until a desired level of noise and inconsistency averaging has been achieved (block 232). Additional impurities may then be scanned and added to the library as desired (block 234).

Figure 12C:
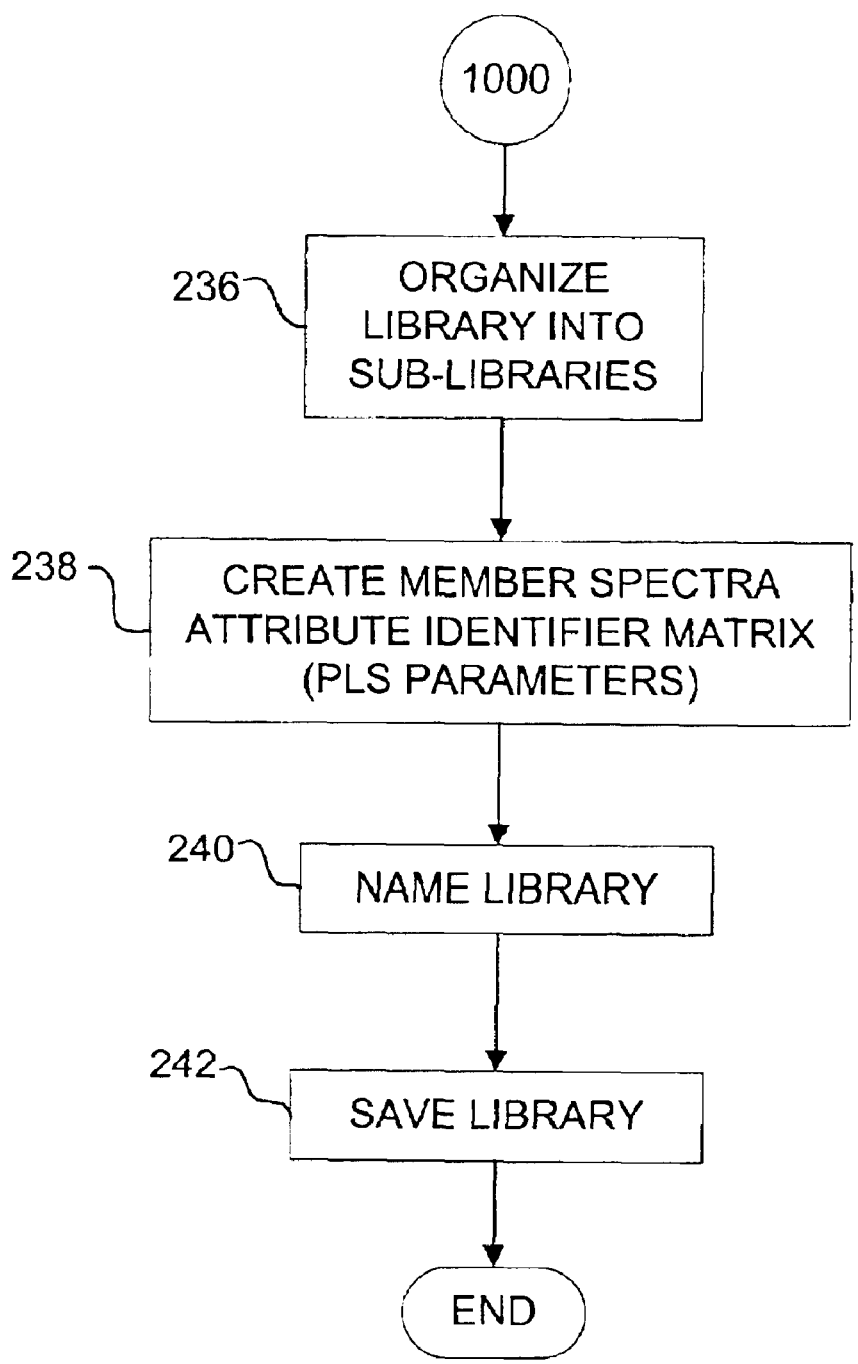
Figure 12D:
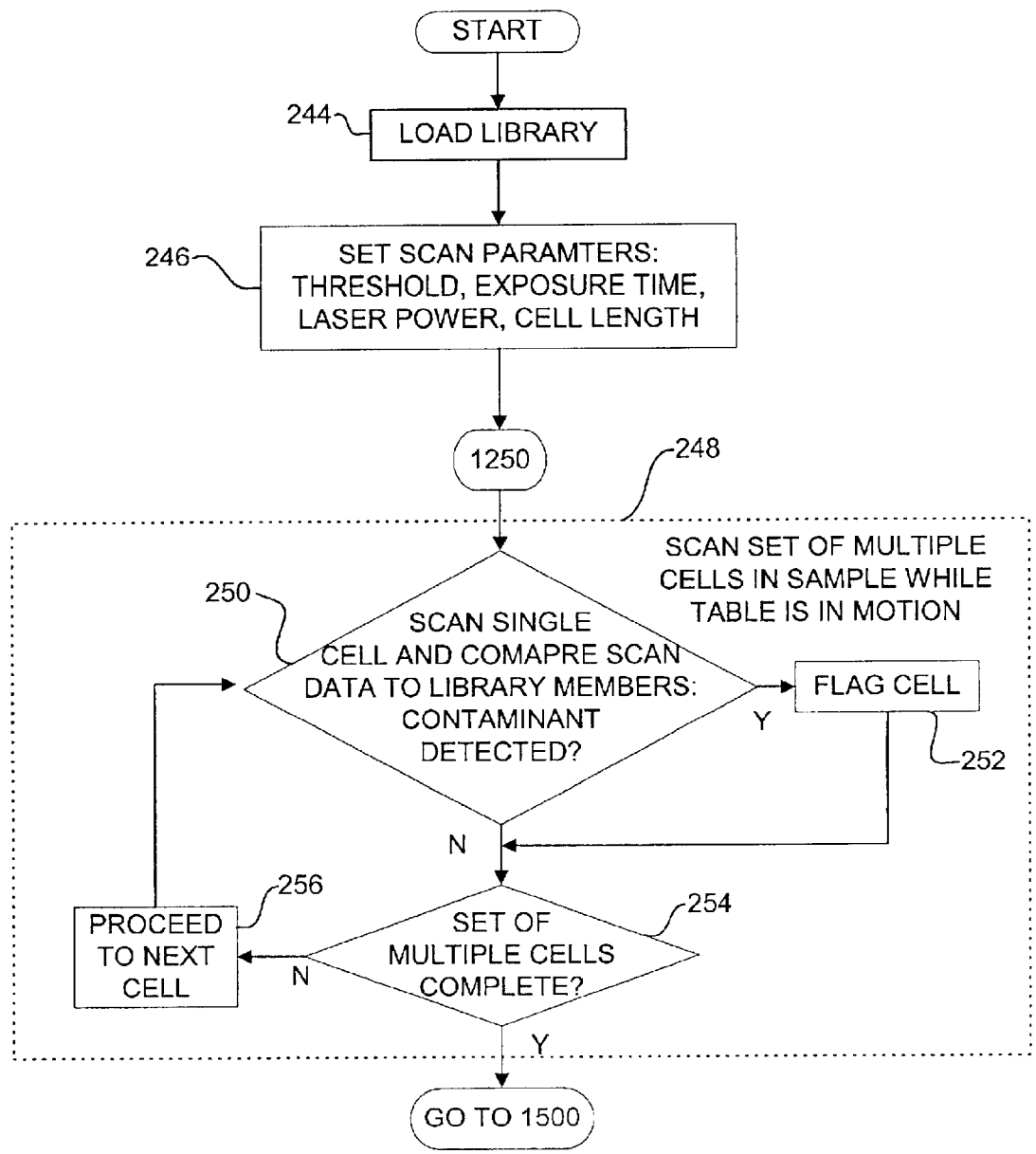

Referencing FIG. 12(c), with all members now placed in the library, the library may be further organized into sub-libraries (block 236). For example, one background data member and a number of contaminant data members that may have a high probability of occurring with one another may be placed in a single sub-library. This sub-library can be more quickly searched than the entire library, so that when circumstances suggest that one of the sub-library impurities may be encountered time savings can be achieved.

Library data member attribute identifiers are also created (block 238). As used herein, the term "attribute identifiers" is intended to broadly refer to a data set used to identify and characterize the data member. Preferably, a table or matrix is created that provides information about the data member, but that is smaller and thus easier to search and review than the data member itself. Most preferably, a partial least squares ("PLS") characterization of the spectra data is created. The library is then named and saved (blocks 240–242).

After at least one library has been created and is available for use, samples may be scanned for impurities. To do so, a library is first loaded (block 244). Scan parameters for the spectrometer are then set (block 246). "Scan parameters" as used herein is intended to broadly refer to control settings for the spectrometer apparatus, including but not limited to the spectrometer laser and X-Y table. Preferably, these parameters comprise at least a threshold, exposure time, laser power, and cell length. A threshold may be thought of as a baseline contaminant detection sensitivity. That is, a threshold generally comprises the distance from the "pure" background that a scan must be before a determination is made that a contaminant has been detected. Exposure time and laser power depend to an extent on one another, and function to generally control the total energy used to illuminate the sample. That is, the energy available from a spectrometer light source is generally a constant, but can be varied by lowering power and extending exposure time or vice-versa. Cell length refers to the size of the area to be sampled by the spectrometer. These settings may additionally depend on or include speed of sample conveyance.

Once these settings are complete, scanning of the sample can begin. Generally, scanning is performed in a first continuous scan mode (dashed line box 248) with the sample table being generally continuously moved with scanned cells determined to contain a contaminant "flagged" for later intermittent or slow scanning. As will be appreciated by those knowledgeable in the art, to "flag a cell" as used herein is intended to refer to marking, recording, or otherwise identifying a cell. In the continuous mode, each cell may be scanned, or a representative pattern or sampling of the cells scanned.

It has been discovered that a continuous scanning followed by intermittent scanning sequence achieves time savings through scan table movement efficiencies, data processing efficiencies, and other ways. For example, table motion related time savings are achieved in that the sample table may be kept in substantially continuous motion through the initial continuous scan mode, thereby eliminating time required for table motion stopping and starting. Data processing savings are achieved in that "quick" comparisons of scan images to library data members may be made during the initial continuous mode to determine if a cell differs from the background data member by more than the threshold. More detailed comparisons of flagged cells are then made in the subsequent intermittent or "slow" scan mode. That is, in the continuous scan mode a determination is made after each cell has been scanned as to whether a contaminant has been detected in the cell by comparing the integrated scan data from the cell with the library member background data member (block 250). Data may be compared in the form of the raw data, the normalized vector data, or preferably in the form of the PSL data for reasons of data processing resource savings. Should scan data from a cell differ from the background data member by more than the threshold, the cell is flagged (block 252). The set of multiple cells is continuously scanned until all desired cells have been scanned (blocks 254–256).

Figure 12E:
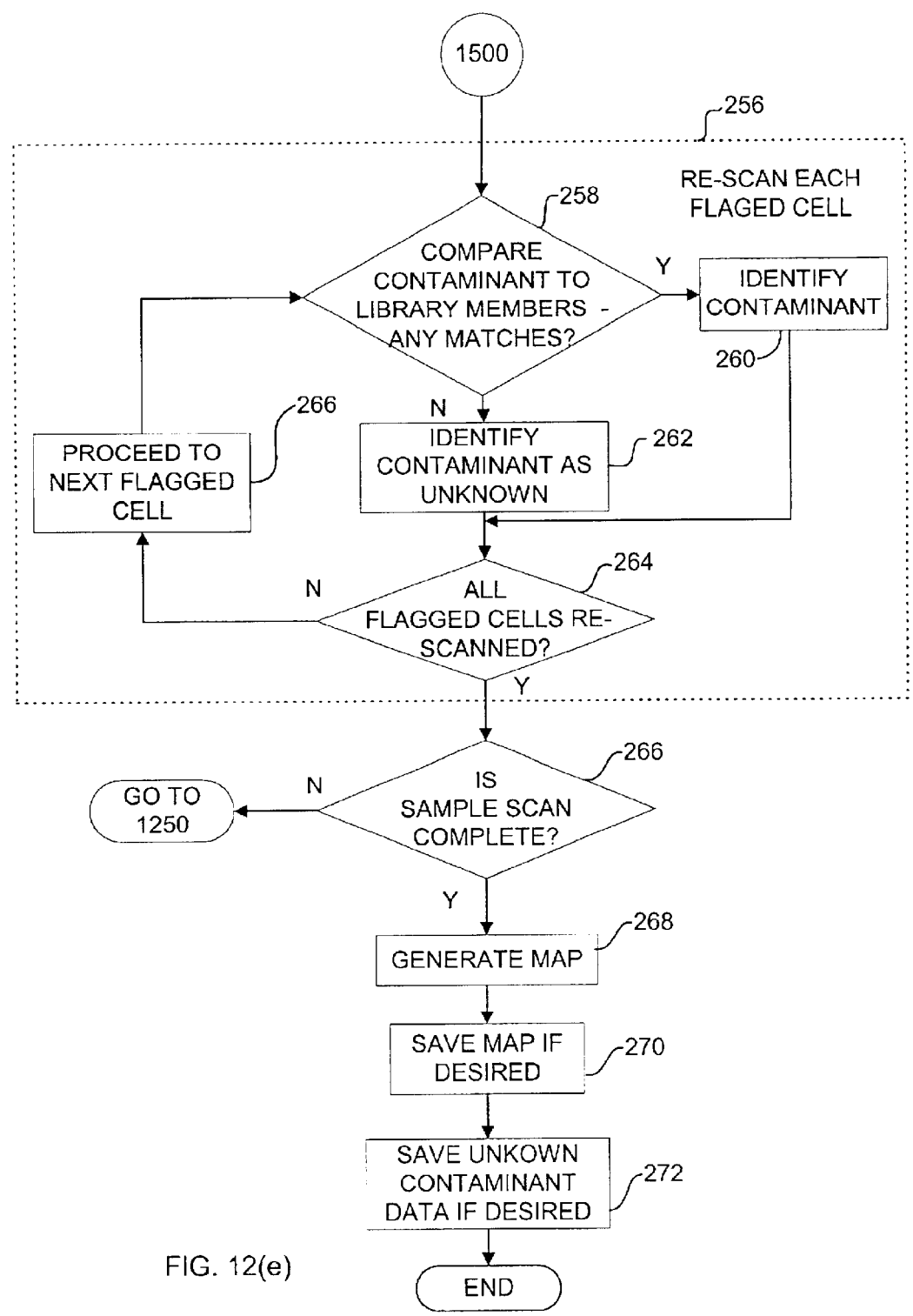

Referring now to FIG. 12(e), the sample table advances back to each flagged zone, with the flagged cells individually re-scanned (dashed line block 256). During re-scanning, the size of the contaminant can be measured. After each cell has been scanned, a comparison is made between the scan data and the library members to determine if the contaminant can be identified (blocks 258–260). If no matching data member is found, the contaminant may be labeled as an "unknown" (block 262). This process continues until all flagged cells have been re-scanned (blocks 264–266). Additional groups of multiple cells can be scanned if desired (block 266).

Also, additional time savings may be achieved by an initial scan of large cells, with the large cell flagged for re-scanning if it is found to contain any material in it that differs from the background fingerprint. The large cell may be, for purposes of illustration, a size on the order of 0.5 by 5 mm. To speed this initial or continuous scan, the library of foreign material fingerprints is not searched for a matching fingerprint, with the cell "flagged" simply on the basis of containing a fingerprint that does not match the background material fingerprint. Each flagged cell will subsequently be subdivided into a plurality of smaller cells that will each be re-scanned to more tightly map the location and nature of the foreign material. Once again for purposes of illustration, the smaller cells may have a size of the order of 0.5 by 0.5 mm. Only during re-scanning is processing time taken to search the known fingerprints from the library of foreign materials for a match.

Upon completion of the scanning, a sample map can be created and saved if desired (blocks 268–270). Preferably, the map is in the format as generally described herein above with reference to FIG. 3, and generally comprises a two dimensional color coded map of the sample with colored portions representing the relative size, position, and identity of impurities in the sample. The map may further provide information regarding the quantity of the impurity. Data such as a fingerprint for any unknown contaminant or material may be stored (block 272) for future identification and/or analysis.

Those knowledgeable in the art will appreciate that the method and program product embodiments discussed herein and illustrated in FIGS. 11 and 12 have been presented for illustration of preferred embodiments only. Modifications, rearrangements and changes can be made without departing from the scope of the invention. For example, the sequence of method or some program product steps could easily be changed within the scope of the invention as claimed. Further, several of the illustrated steps could be combined or separated without altering the functional operation of the invention.

For example, although invention embodiments have been shown and discussed with reference to material detection in paper and pulp, the method and apparatus of the invention are equally applicable to the evaluation and identification of coating compositions and their respective constituents, whether in the form of powders, slurries, coating drawdowns or coatings on paper substrates. The method and apparatus are also useful for detection and identification in paper samples of specific paper additives, such as talc and clay; and for the identification of shives in paper.

Moreover, the method and apparatus of the invention may be utilized to determine the reasons for defects appearing in printed paper products, e.g., non uniform or spotty reception of printing inks caused, for example, by the presence of shives in the paper. The suspect or offending area or spot on the printed sheet may be subjected to Raman interrogation for identification, for example, of the wood species from which the shive(s) emanated, so the offending wood species can be eliminated from future pulp formulations, thereby to avoid repetition of the problem in future paper products.

Additionally, the present invention may be practiced at any of several points in the manufacturing process. In the manufacture of paper products, for instance, sampling may be done on or off line, and with wet or dried pulp or paper. The embodiment of the apparatus of the invention shown and described is generally suitable for off line sampling. However, it is intended that other embodiments may comprise a spectrometer probes configured for scanning an on-line process stream of pulp, coating composition, or other constituents of pulp or paper. An on-line apparatus may comprise diverting a portion of the stream through a Raman scanning station.

The objects and advantages of the invention have therefore been shown to be attained in a convenient, practical, speedy, economical and facile manner. While certain preferred embodiments of the invention have been herein illustrated and described, it is to be appreciated the various changes, rearrangements and modifications may be made therein without departing from the scope of the invention as defined by the appended claims. By way of example, reference has been made herein to practice of embodiments of the method of the invention to detect the presence of stickies, sclereids, and shives. It will be appreciated by those knowledgeable in the art that the invention will also be useful for detection and/or identification of a variety of additional materials.

What is claimed is:

1. A method for identifying materials in a pulp or paper sample comprising the steps of providing a wet pulp or paper sample, translating the sample along plural axes in a selected pattern, scanning the sample with a Raman spectroscope as it is translated along said pattern, comparing Raman spectroscopic images generated by the probe with a library of Raman spectroscopic images of known materials potentially present in the sample, identifying and communicating data on at least one of the materials discerned in the sample, and spectroscopically analyzing characteristics of the sample along a Z-axis of the sample.

2. A method as set forth in claim 1 wherein the steps recited in claim 1 are carried out at speeds sufficient to produce a Raman spectroscopic analysis of the sample within a time frame of about thirty minutes or less based on a sample surface size of at least 64 square inches.

3. A method as set forth in claim 1 wherein the translating and scanning steps are substantially continuous, and said identifying step comprises identifying cells of foreign substances from the desired constituents of the pulp or paper.

4. A method as set forth in claim 3 further comprising the steps of translating and scanning the identified cells of foreign substances in the sample, and identifying and communicating data on at least one of the foreign substances discerned in the sample.

5. A method as set forth in claim 4, further comprising the step of generating a map of the foreign substances discerned in the sample.

6. A method as set forth in claim 1 wherein said library of Raman spectroscopic images of known materials comprises contaminant images, and wherein said step of identifying and communicating data includes determining the size of at least one contaminant material discerned in the sample.

7. A method as set forth in claim 1 further comprising the step of providing the pulp or paper sample on-line in a pulp or papermaking process.

8. A computer program product for causing a spectrometer apparatus to detect impurities in a pulp or paper sample, the program product comprising computer readable instructions embedded in a computer readable medium that when executed by a computer cause the spectrometer apparatus to:

scan at least one background sample with the spectrometer, store a resultant background data member in a library;

scan at least one contaminant sample with the spectrometer, store a resultant contaminant data member in said library;

divide the sample into a plurality of cells, convey the sample while scanning said plurality of sample cells with the spectrometer, compare scan data from said sample scan of each of said plurality of cells with said background data member, flag each cell having a scan differing from said background data member; and re-scan each of said flagged cells and compare resultant scan data with said contaminant data members.

9. A computer program product as set forth in claim 8, further comprising the step of converting raw scan data to normalized vector data.

10. A computer program product as set forth in claim 8, wherein said program instructions when executed cause the spectrometer apparatus to convey the sample along an X and Y-axis orientation, and wherein said program instructions when executed further cause the spectrometer apparatus to output data comprising a relative location of contaminants with reference to said X and Y-axis orientation.

* * * * *